US00PP19527P2

(12) United States Plant Patent
Bradford

(10) Patent No.: US PP19,527 P2
(45) Date of Patent: Dec. 2, 2008

(54) PLUM TREE NAMED 'BLACK MAJESTY'

(50) Latin Name: *Prunus persica*
Varietal Denomination: Black Majesty

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,890

(22) Filed: Nov. 26, 2007

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

PP2,747 P 6/1967 Bradford
PP14,220 P2 10/2003 Bradford

*Primary Examiner*—Annette H Para
*Assistant Examiner*—S. B. McCormick-Ewoldt

(57) ABSTRACT

The present invention relates to an plum tree and more particularly to a new and distinct variety broadly characterized by a medium size, vigorous, hardy, and very productive tree. Being self-unfruitful, the present variety requires cross pollination from a plum that blooms during the mid season. The present variety's abundance of blossoms and pollen entices strong bee activity to facilitate pollination. The fruit matures under the ecological conditions described during early September, with first picking on Sep. 2, 2007, and will hang on the tree for about fifteen more days. The fruit is uniformly medium in size, nearly black in skin color, clingstone in type, globose with a small point at the apex shape, orange yellow in flesh color, firm in texture, and very sweet in flavor.

1 Drawing Sheet

Botanical classification: *Prunus persica.*
Varietal denomination: 'Black Majesty'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Black Majesty'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 1998 one such house containing an unpatented purple plum, code named 42P1156, was crossed by me in this manner. To pollinate this purple plum, I selected bouquets from several sources of plum and interspecific trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2003 the claimed variety was selected by me as a single plant from the group of seedlings described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'Angeleno' (U.S. Plant Pat. No. 2,747) plum by being self-unfruitful and by producing fruit that is mostly black in skin color, that is clingstone in type, and that ripens near the first of September, but is distinguished therefrom by being easier to pollinate, by being more consistent in production, and by producing fruit that is much sweeter in flavor and that possesses and maintains much more juice.

SUMMARY OF VARIETY

The present plum variety is characterized by a medium size, vigorous, hardy, and productive tree. Being self-unfruitful, the present variety requires cross pollination from a plum that blooms during the mid season. The present variety's abundance of blossoms and pollen entices strong bee activity to facilitate pollination. The fruit matures under the ecological conditions described during early September, with first picking on Sep. 2, 2007, and will hang on the tree for about fifteen more days. The fruit is uniformly medium in size, nearly black in skin color, clingstone in type, globose with a small point at the apex shape, orange yellow in flesh color, firm in texture, and very sweet in flavor.

DRAWING

The accompanying photograph consists of four whole fruits positioned to display the characteristics of the skin color and form, two half fruits divided to reveal the flesh and stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Sep. 15, 2007, on the original tree during its ninth growing season. The flower and bud descriptions were developed during the previous blooming season. All major color code designations are by reference to the Inter-Society Color Council, National Bureau of Standards. Common color names are also used occasionally.

Parentage

Seed parent: 42P1156 plum (unpatented).
Pollen parent: Unknown.

Tree

Size: Medium, reaching and maintaining a height of 12' [3.66 m.] and a spread of 8' [2.44 m.] after nine growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming plum such as 'September YUMMY' (U.S. Plant Pat. No. 14,220).

Bearing: Very consistent with no crop failures observed.

Trunk:

- *Size.*—Medium, reaching a maximum diameter of 5" [127 mm.] after the ninth growing season.
- *Texture.*—Shaggy.
- *Bark color.*—A Dark yellowish brown [78. d.yBr] and Moderate reddish brown [43. m.rBr] variegation with Dark orange yellow [72. d.OY] crevices present.
- *Lenticels.*—Approximate Number Per Square Inch: 5. Color: Dark orange yellow [72. d.OY]. Average Size: ¼" [6.4 mm.]. Shape: Eye-shaped, elongated.

Branches:

- *Size.*—Diameter of limb is 1¼" [32 mm.] measured 12" from central leader.
- *Texture.*—Smooth on first and second year wood, increasing roughness with age.
- *Color.*—1st Year Wood Topside: Moderate yellowish brown [77. m.yBr]. 1st Year Wood Underside: Moderate olive [107. m.Ol]. Older Wood: Dark yellowish brown [78. d.yBr].
- *Lenticels.*—Number Per Square Inch: More than 60 on second year wood. Color: Dark orange yellow [72. d.OY]. Average Size: 1/16" [1.6 mm.]. Shape: Elongated, rectangular.

Leaves:

- *Size.*—Medium. Average Length: 3½" [89 mm.]. Average Width: 1⅝" [41 mm.].
- *Arrangement.*—Alternate.
- *Thickness.*—Medium.
- *Form.*—Elliptical.
- *Apex.*—Mucronate to acuminate.
- *Base.*—Acute with an average angle base angle of 60 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ⅜" [9.5 mm.]. Average Thickness: 1/16" [1.6 mm.]. Color: Very yellow green [115. v.YG].
- *Stipules.*—Number: 2 per leaf, up to 6 per growing tip. Average Length: ¼" [6.4 mm.]. Color: Light yellow green [119. l.YG] becoming Deep reddish brown [41. deep rBr] with age.
- *Glands.*—Number: Average of 2 to 4 per leaf. Position: Alternately positioned at the intersection of the petiole and the leaf blade. Size: Medium. Form: Globose. Color: Deep yellowish green [132. deep yG] becoming Dark brown [59. d.Br] in the center with age. Leaf buds: Pointed, medium.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.

- *Average flower diameter.*—1" [25.4 mm.].
- *Number of petals.*—Five, no double blossoms observed.
- *Petal shape.*—Oval to circular.
- *Petal margin.*—Entire, smooth to slightly wavy.
- *Average petal diameter.*—½" [12.7 mm.].
- *Average petal length.*—9/16" [14.3 mm.].
- *Petal apex.*—Rounded.
- *Petal base.*—Obtuse.
- *Petal color.*—White [263. White] on both sides.
- *Anther color.*—Brilliant orange yellow [67. brill.OY].
- *Stigma color.*—Brilliant greenish yellow [98. brill.gY].
- *Sepal color.*—Brilliant yellow green [116. brill.YG] on the outer surface.
- *Sepal length.*—5/32" [4.0 mm.].
- *Sepal width.*—5/32" [4.0 mm.].
- *Sepal apex.*—Rounded to elliptical to match the width and length.
- *Sepal margin.*—Fairly smooth.
- *Average pistil length.*—⅝" [15.9 mm.].
- *Average stamen length.*—½" [12.7 mm.].
- *Fragrance.*—Moderate.
- *Pollen production.*—Strong, very enticing to bees.

*Blooming period.*—Medium, with 'Santa Rosa' plum (unpatented).
*Onset of bloom.*—One percent on Feb. 28, 2007.
*Date of full bloom.*—Mar. 6, 2007.
*Duration of bloom.*—One to two weeks, dependent on ambient temperature.
*Bloom density.*—Very heavy.
*Number per cluster.*—2 to 10, usually 2 or 3.

FRUIT

Maturity when described: Firm ripe, Sep. 15, 2007.
Date of first picking: Sep. 2, 2007.
Date of last picking: Sep. 15, 2007.
Size: Uniform, Medium.
*Average diameter axially.*—2⅜" [60.3 mm.].
*Average diameter across cheek plane.*—2 7/16" [61.9 mm.].
*Average diameter across suture plane.*—2⅜" [60.3 mm.].
*Typical weight.*—4.9 ounces [139 grams].
Form: Uniform, globose, symmetrical.
*Longitudinal section form.*—Round to cordate.
*Transverse section through diameter.*—Round.
Suture: A inconspicuous line located in a very shallow groove extending from the base just to the apex.
Ventral surface: Rounded, slightly lipped toward the base.
Lips: Equal.
Cavity: Rounded, suture showing on one side.
*Depth.*—5/16" [7.9 mm.].
*Breadth.*—¾" [19.1 mm.].
Base: Truncate.
Apex: Rounded and typically mammiform.
Pistil point: An inconspicuous dot located at the tip of the apex.
Stem: Medium.
*Average length.*—⅜" [9.5 mm.].
*Average width.*—5/64" [2.0 mm.].
Skin:
*Thickness.*—Medium.
*Surface.*—Smooth.
*Tenacity.*—Tenacious to the flesh.
*Astringency.*—Slight.
*Tendency to crack.*—None observed.
*Color.*—Blackish red [21. blackish R] with very small Moderate reddish brown. [43. m.rBr] freckling throughout.
*Bloom.*—Abundant.
Flesh:
*Color.*—Deep orange yellow [69. deep OY].
*Surface of pit cavity.*—Covered with Moderate orange yellow [71. m.OY] fibers when twisted away from the stone.
*Amygdalin.*—Slight.
*Juice.*—Moderate, rich.
*Texture.*—Firm, crisp to meaty.
*Fibers.*—Abundant, fine, tender.
*Ripens.*—Slightly earlier toward the apex.
*Flavor.*—Very sweet with only slight acid, typically 23 brix.
*Aroma.*—Moderate.
*Eating quality.*—Very good.

STONE

Type: Clingstone.
Form: Oval.
Hilum: Narrow.
Base: Straight.
Apex: Acuminate, with a sharp 1/16" [1.6 mm.] tip.
Sides: Equal.
Surface: Rough throughout, a few vertical grooves toward the base, one groove from base to apex on each side of the dorsal fin.
External color of stone: Dark orange yellow [72. d.OY].
Pit wall color when cracked: Deep yellow [85. deep Y].
Cavity surface color: Moderate olive brown [95. m.OlBr].
Average pit wall thickness: 1/16" [1.6 mm.].
Average width: ⅝" [15.9 mm.].
Average length: 15/16" [23.8 mm.].
Average breadth: ⅜" [9.5 mm.].
Tendency to split: None observed.
Kernel:
*Form.*—Oval.
*Skin color.*—Pale yellow [89. p.Y] when first cracked.
*Pellicle color.*—Moderate olive [107. m.Ol].
*Vein color.*—Moderate olive [107. m.Ol].
*Taste.*—Bitter.
*Viable.*—Yes.
*Average width.*—7/16" [11.1 mm.].
*Average length.*—9/16" [14.3 mm.].
*Amygdalin.*—Moderate.

Use

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is similar to 'Angeleno' (U.S. Plant Pat. No. 2,747) plum by being self-unfruitful and by producing fruit that is mostly black in skin color, that is clingstone in type, and that ripens near the first of September, but is distinguished therefrom by being easier to pollinate, by being more consistent in production, and by producing fruit that is much sweeter in flavor and that possesses and maintains much more juice.

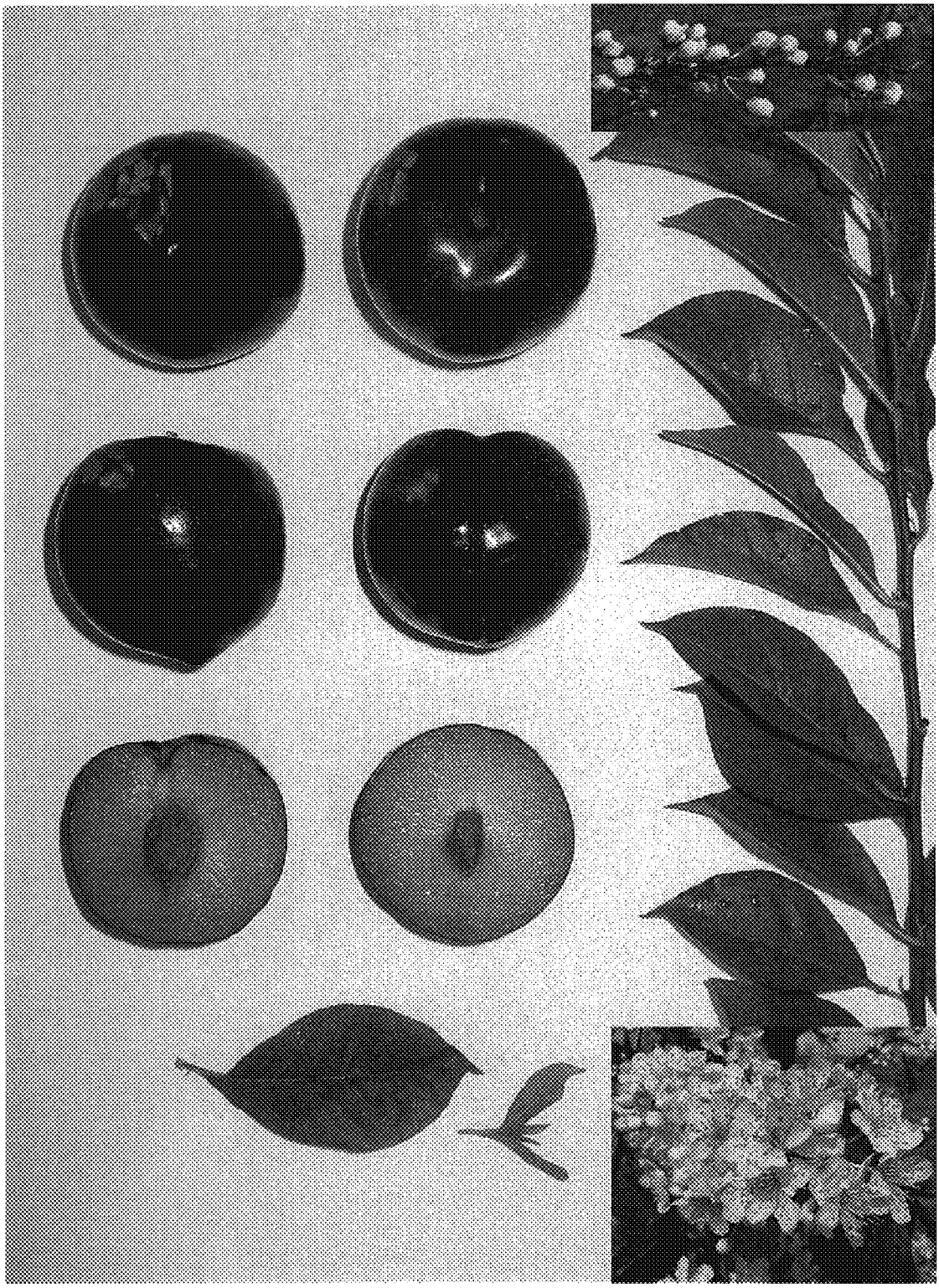

* * * * *